(12) United States Patent
Taba et al.

(10) Patent No.: US 10,067,044 B2
(45) Date of Patent: Sep. 4, 2018

(54) AIRCRAFT STRENGTH TESTING APPARATUS AND AIRCRAFT STRENGTH TESTING METHOD

(71) Applicant: MITSUBISHI AIRCRAFT CORPORATION, Aichi (JP)

(72) Inventors: Shunsuke Taba, Tokyo (JP); Toshio Nakamura, Tokyo (JP); Kaoru Tsukigase, Aichi (JP); Keisuke Kumagai, Aichi (JP); Toshiyasu Fukuoka, Aichi (JP)

(73) Assignee: MITSUBISHI AIRCRAFT CORPORATION, Aichi (JP)

( * ) Notice: Subject to any disclaimer, the term of this patent is extended or adjusted under 35 U.S.C. 154(b) by 74 days.

(21) Appl. No.: 15/111,019

(22) PCT Filed: Dec. 24, 2014

(86) PCT No.: PCT/JP2014/006426
§ 371 (c)(1),
(2) Date: Jul. 12, 2016

(87) PCT Pub. No.: WO2015/140863
PCT Pub. Date: Sep. 24, 2015

(65) Prior Publication Data
US 2016/0377517 A1    Dec. 29, 2016

(30) Foreign Application Priority Data

Mar. 17, 2014   (JP) .................................. 2014-053955

(51) Int. Cl.
*B64F 5/60*        (2017.01)
*B64C 1/06*        (2006.01)
(Continued)

(52) U.S. Cl.
CPC ............... *G01N 3/12* (2013.01); *B64C 1/061* (2013.01); *B64C 1/064* (2013.01); *B64C 1/12* (2013.01); *G01M 5/0075* (2013.01); *G01N 3/08* (2013.01)

(58) Field of Classification Search
CPC ........... B64C 1/06; B64C 1/061; B64C 1/064; B64C 1/12; G01M 5/0075; G01N 3/08; G01N 3/12; B64F 5/60
See application file for complete search history.

(56) References Cited

U.S. PATENT DOCUMENTS 2,151,584 A * 3/1939 Bugatti ............... G01M 5/0016
                                                    73/583
2,383,491 A * 8/1945 Kemmer ............. G01M 5/0016
                                                    73/798
(Continued)

FOREIGN PATENT DOCUMENTS

JP           04351936 A  * 12/1992
JP      H05-043406 Y2     11/1993
(Continued)

OTHER PUBLICATIONS

Extended European Search Report for EP Application No. 14886567.8 dated Sep. 18, 2017.
(Continued)

*Primary Examiner* — Nguyen Ha
(74) *Attorney, Agent, or Firm* — Pearne & Gordon LLP

(57) ABSTRACT

To provide an aircraft strength testing apparatus that, using a curved specimen, can produce a desired stress safely and quickly by reliably applying an internal pressure, and moreover allows any resulting damage to be reliably observed. A testing apparatus 1 that applies an internal pressure, equivalent to a differential pressure between the outside and the inside of a section to be tested of a fuselage of an aircraft, to a curved specimen 10 corresponding to the section to be
(Continued)

tested, includes: a pressure vessel 22 between which and the specimen 10 a cavity 23 is formed; and rods 25 that restrain the specimen 10 against the internal pressure. The pressure vessel 22 faces the outer side of the specimen 10. By reducing the pressure inside the cavity 23, an internal pressure is applied to the specimen 10.

20 Claims, 10 Drawing Sheets

(51) Int. Cl.
*B64C 1/12* (2006.01)
*G01N 3/12* (2006.01)
*G01N 3/08* (2006.01)
*G01M 5/00* (2006.01)

(56) References Cited

U.S. PATENT DOCUMENTS

| | | | | |
|---|---|---|---|---|
| 2,647,399 A | * | 8/1953 | Newbill, Jr. | G01M 5/005 |
| | | | | 428/319.1 |
| 3,945,249 A | | 3/1976 | Knoth | |
| 4,453,413 A | | 1/1984 | Schneider | |
| 4,976,136 A | * | 12/1990 | Willan | G01M 3/20 |
| | | | | 73/40.7 |
| 5,065,630 A | | 11/1991 | Hadcock et al. | |
| 5,257,088 A | * | 10/1993 | Tyson, II | G01B 11/161 |
| | | | | 244/125 |
| 5,404,747 A | * | 4/1995 | Johnston | G01M 3/24 |
| | | | | 73/40 |
| 7,246,527 B2 | | 7/2007 | Ostgaard | |
| 2003/0037604 A1 | * | 2/2003 | Poblete | G01M 3/2869 |
| | | | | 73/73 |
| 2004/0035979 A1 | * | 2/2004 | McCoskey, Jr. | B64C 1/12 |
| | | | | 244/117 R |
| 2006/0101921 A1 | | 5/2006 | Ostgaard | |
| 2010/0313670 A1 | | 12/2010 | Decraecker | |

FOREIGN PATENT DOCUMENTS

| | | |
|---|---|---|
| JP | 2004-245774 A | 9/2004 |
| JP | 2006-038634 A | 2/2006 |
| JP | 5306339 B2 | 10/2013 |

OTHER PUBLICATIONS

International Search Report issued in Application No. PCT/JP2014/006426 dated Mar. 31, 2015.

* cited by examiner

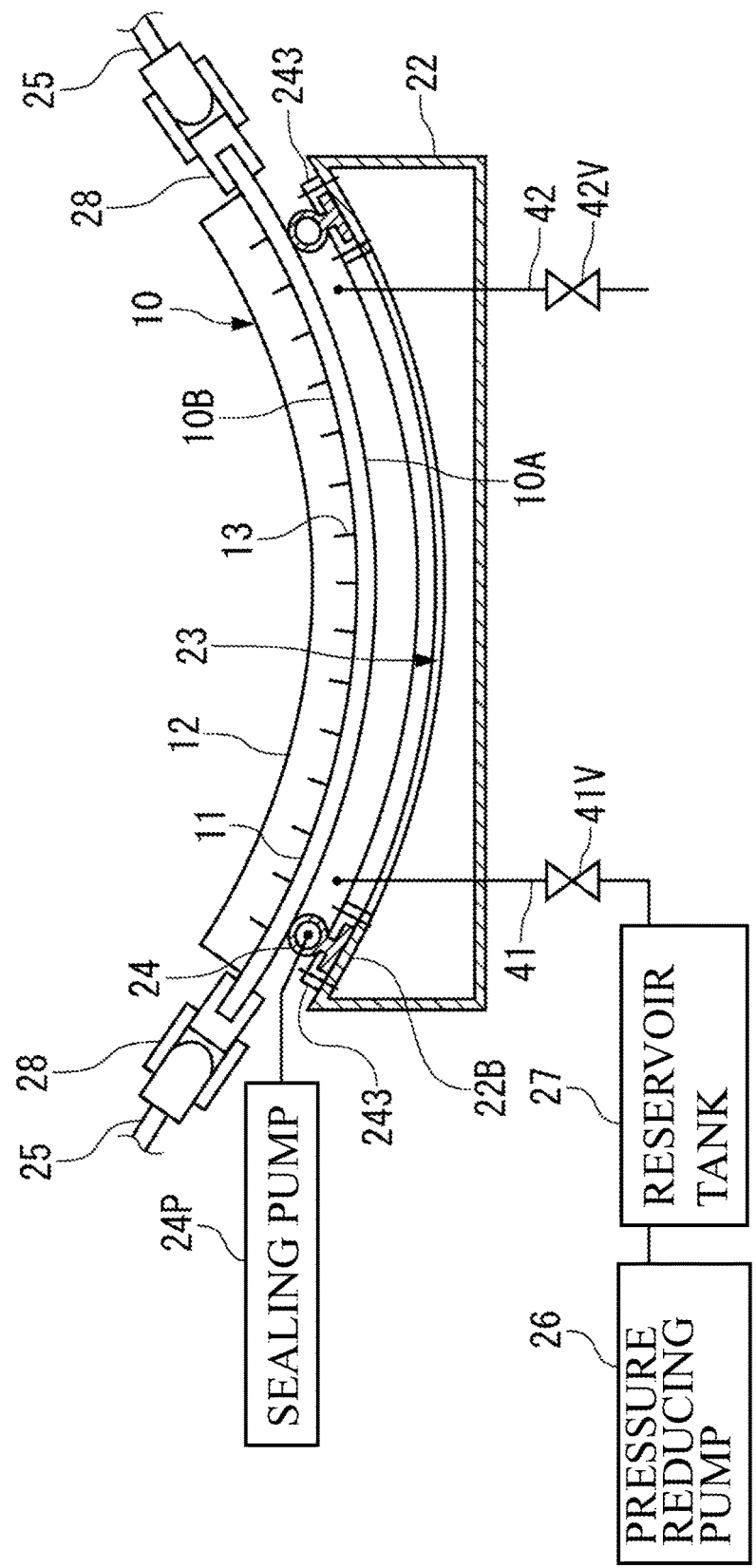

--Prior Art--

AIRCRAFT STRENGTH TESTING APPARATUS AND AIRCRAFT STRENGTH TESTING METHOD

TECHNICAL FIELD

The present invention relates to an apparatus and a method for testing the strength of the airframe of an aircraft using a curved specimen.

BACKGROUND ART

A strength test is performed in which a differential pressure and bending that occur in the sky are input into a specimen of the fuselage etc. of an aircraft.

As part of the strength test, an internal pressure test is performed in which the inside of a specimen (barrel) of a cylindrical fuselage panel structure is pressurized.

Since the cylindrical fuselage panel structure is a huge structure, not only is the production cost of the specimen high, but also a large space is required to install a testing device on which the specimen is set. Moreover, due to the time taken to raise the pressure of the cylindrical space inside the specimen to a required pressure, it takes an enormous amount of time to obtain results of a fatigue strength test after repeated pressurization and pressure release into the atmosphere.

Therefore, the test may be performed on a partial specimen that corresponds to a part in need of testing of a fuselage panel structure in the circumferential direction, such as a portion where there is an opening (Patent Literature 1).

FIG. 10 schematically shows an internal pressure testing device 9 that applies an internal pressure to a curved partial specimen 91.

The partial specimen 91 has a skin 92 forming the surface of a fuselage, frames 93 supporting the skin 92, and stringers 94 reinforcing the skin 92. The frames 93 and the stringers 94 are internal structural members provided on the inner side of the skin 92.

The internal pressure testing device 9 includes a pressure vessel 96 between which and the inner side of the partial specimen 91 a cavity 95 is formed, and rods 97 that restrain the partial specimen 91 against an internal pressure applied thereto. As the cavity 95 is injected with air and pressurized, an internal pressure equivalent to the differential pressure between the outside air pressure and the cabin pressure during flight acts on the partial specimen 91. A sealing member 98 that seals the cavity 95 is disposed annularly between the partial specimen 91 and the pressure vessel 96.

CITATION LIST

Patent Literature

Patent Literature 1: U.S. Pat. No. 7,246,527

SUMMARY OF INVENTION

Technical Problem

Regardless of whether a whole specimen (barrel) or a partial specimen is used, the internal pressure test has been hitherto performed exclusively by pressurizing the cavity located on the inner side of the specimen.

However, in the course of our studies, the present inventors have found the following problems in conducting the internal pressure test:

Firstly, the pressure inside the cavity may become too high and burst the specimen.

Secondly, since the inner side of the specimen is located on the cavity side, it is difficult to observe the development of any resulting damage (cracks etc.) in the specimen. To observe the inner side of the specimen where the starting point of damage commonly lies, it is necessary to dispose a camera inside the cavity or provide the pressure vessel with an observation window.

Thirdly, the volume of the cavity cannot be reduced beyond a certain limit even when a partial specimen is used, let alone when a barrel is used, so that producing a required internal pressure takes a significant time. Due to the presence of the internal structural members (frames and stringers) on the inner side of the partial specimen, a predetermined interval is inevitably left between the partial specimen and the pressure vessel, and a cavity of a considerable volume is formed in that interval.

Fourthly, reliably sealing the gap between the partial specimen and the pressure vessel involves an increase in size of the structure.

To avoid breakage of the seal due to pressurization inside the cavity, a large jig (see the jig 99 in FIG. 10) that presses the specimen against the pressure vessel is required.

Fifthly, the absence of the internal structural members in the peripheral edge portion of the specimen affects the stress distribution in the specimen.

Since the sealing member needs to be installed on a flat surface, the portion of the specimen where the sealing member is installed is not provided with the internal structural members. Accordingly, if that portion of the skin, where the internal structural members are not provided, deforms so as to expand in the out-of-plane direction of the skin due to a pressure rise inside the cavity, it is no longer possible to produce a desired stress evenly in the circumferential direction.

On the basis of the above problems, the present invention aims to provide an aircraft strength testing apparatus that, using a curved specimen, can produce a desired stress safely and quickly by reliably applying an internal pressure, and moreover allows any resulting damage to be reliably observed.

Solution to Problem

The present invention is a testing apparatus that applies an internal pressure, equivalent to a differential pressure between the outside and the inside of a section to be tested of an airframe of an aircraft, to a curved specimen corresponding to the section to be tested, the testing apparatus including: a pressure vessel between which and the specimen a cavity is formed; and a restraining member that restrains the specimen against the internal pressure.

In the present invention, the pressure vessel faces the outer side of the specimen, and an internal pressure is applied to the specimen by reducing the pressure inside the cavity.

In the present invention, the outer side of the specimen corresponds to the outer side of the section to be tested, and the inner side of the specimen corresponds to the inner side of the section to be tested.

Since the pressure inside the cavity is reduced in the present invention, even when the pressure is reduced to the lowest level possible, the maximum pressure reduction is no more than 1 atm. Thus, without such pressure as to burst the specimen produced inside the cavity, the test can be performed safely.

Since the outer side of the specimen faces the pressure vessel and the inner side of the specimen is exposed to the outside of the pressure vessel, the development of any resulting damage on the inner side of the specimen is easy to be visually observed.

Moreover, it is possible to reduce the volume of the cavity by bringing the specimen and the pressure vessel close to each other, since the smooth outer side of the specimen faces the pressure vessel and the internal structural members do not prevent the reduction of the volume of the cavity. Thus, the time required to apply an internal pressure can be reduced.

In addition, when the pressure inside the cavity is reduced, a force acts in a direction of narrowing the interval between the specimen and the pressure vessel, which causes the sealing member sealing the cavity to be pressed against the specimen and the pressure vessel. Thus, the inside of the cavity can be reliably sealed.

Moreover, since the sealing member is disposed on the outer side of the specimen, the position where the sealing member is provided is not restricted by interference with the internal structural members of the specimen.

Furthermore, the present invention can reduce the device cost, since it can use a pressure reducing pump less expensive than a compressor that is commonly used when applying an internal pressure to a specimen by pressurizing the inside of a cavity located on the inner side of the specimen.

It is preferable that the aircraft testing apparatus of the present invention includes: a pressure reducing pump that reduces the pressure inside the cavity by suctioning; a tank provided on a suction path connecting the pressure reducing pump to the cavity; and a valve that is located between the tank and the cavity, and opens and closes the suction path.

If the above configuration is adopted and the pressure reducing pump is operated with the valve closed even while the pressure inside the cavity is not being reduced, the pressure developed by pressure reduction is accumulated inside the tank.

Then, when the valve is opened, the pressure inside the cavity is rapidly reduced by the pressure inside the tank, and thus the time required to reduce the pressure to a specified pressure can be reduced.

By using a pressure reducing pump of a popular product of which the suction capacity is not so high, it is possible to secure the sufficient suction capacity to reduce the pressure inside the cavity within a predetermined time while keeping down the cost.

In the aircraft testing apparatus of the present invention, it is preferable that a sealing member that seals the cavity is disposed between the specimen and the pressure vessel, and that the inside of the sealing member is filled with a gas at a predetermined pressure.

Then, the sealing member can be brought into close contact with the specimen and the pressure vessel by virtue of the repulsive force of the gas, and thus the cavity can be sealed more reliably.

It is preferable that the aircraft testing apparatus of the present invention includes a support member that supports the restraining member, and that the restraining member is coupled with a pin to the support member.

Since the restraining member (e.g., rod) is coupled with a pin and can turn relative to the support member, a bending stress in the out-of-plane direction is less likely to occur on the specimen. Accordingly, a desired stress distribution can be reproduced over the entire region of the specimen facing the cavity.

It is preferable that the aircraft testing apparatus of the present invention includes a support member that supports the restraining member, and that a side supported by the support member in the restraining member is movable in the out-of-plane direction of the specimen (the direction intersecting with the plane of the specimen).

The bending stress in the out-of-plane direction on the specimen can be dissipated by the restraining member (e.g., rod) shifting during application of an internal pressure, so that a desired stress distribution can be reproduced.

In the aircraft testing apparatus of the present invention, it is preferable that the specimen includes a skin, a frame supporting the skin, and a stringer reinforcing the skin; that a sealing member that seals the cavity is disposed in a peripheral edge portion on the outer side of the skin; and that, of the frame and the stringer, at least the frame is present at a position on the inner side of the skin corresponding to the position of the sealing member.

Since the sealing member is disposed on the outer side of the specimen in the present invention, it is not necessary that the frames and the stringers are absent, and the frames and the stringers can be provided over the entire region of the specimen to which an internal pressure is applied. Thus, it is possible to produce a desired stress on the specimen without causing the peripheral edge portion of the skin to expand in the out-of-plane direction.

It is preferable that the aircraft testing apparatus of the present invention includes a device that applies an axial force along an axis to the specimen that is formed in a circular arc shape in cross-section around the axis.

Then, it is possible to produce a combined stress field, based on that of an actual aircraft, on the specimen by applying both an internal pressure and an axial force thereto.

The present invention also provides an aircraft strength testing method using the above specimen.

A first testing method includes an internal pressure application step of applying an internal pressure, equivalent to a differential pressure between the outside and the inside of the section to be tested, to the specimen by applying a negative pressure to the inside of a cavity faced by the outer side of the specimen.

A second testing method includes: the above internal pressure application step; and a pressure release step of returning the pressure inside the cavity, to which the negative pressure has been applied, to an atmospheric pressure or a pressure close to the atmospheric pressure, wherein one cycle including at least the internal pressure application step and the pressure release step is repeated a predetermined number of times of cycles.

Advantageous Effects of Invention

According to the present invention, it is possible to produce a desired stress safely and quickly using a curved specimen by reliably applying an internal pressure to the specimen, and moreover to reliably observe any resulting damage in the specimen.

BRIEF DESCRIPTION OF DRAWINGS

FIG. 3 is a partially enlarged view of FIG. 2, with auxiliaries of the testing apparatus shown therewith.

DESCRIPTION OF EMBODIMENTS

In the following, an embodiment of the present invention will be described with reference to the accompanying drawings.

Figure 1:
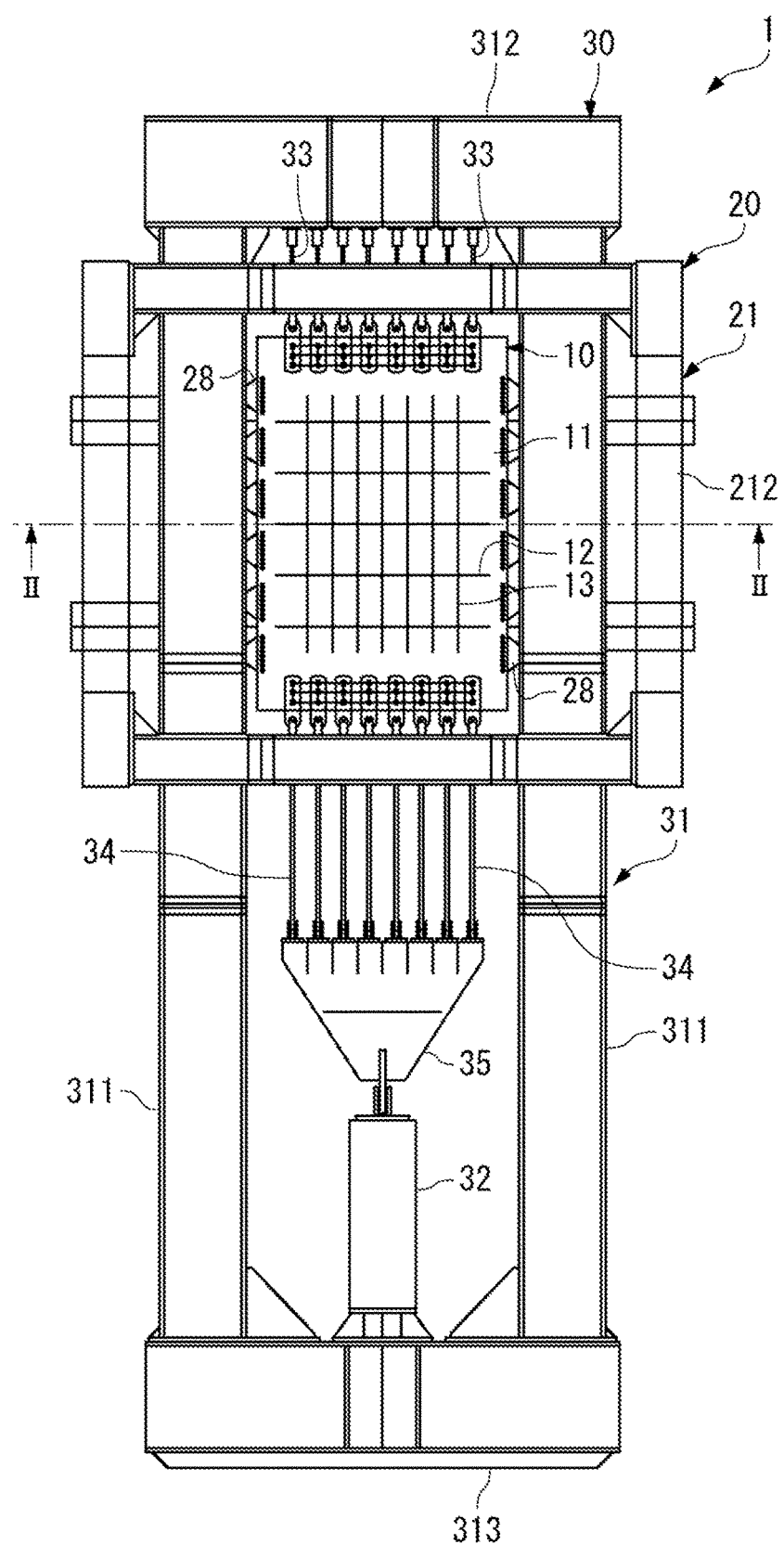
FIG. 1 is a plan view of a combined load testing apparatus according to an embodiment of the present invention.

A combined load testing apparatus 1 shown in FIG. 1 can, using a curved specimen 10, test the static strength, fatigue strength, and damage tolerance of the fuselage structure of an aircraft.

The combined load testing apparatus 1 includes an internal pressure testing device 20 that applies an internal pressure to the specimen 10 and an axial force testing device 30 that applies an axial force in a tensile direction to the specimen 10, and can produce a combined stress field on the specimen 10 by applying both an internal pressure and an axial force.

The internal pressure testing device 20 and the axial force testing device 30 constitute independent force systems between which no exchange of forces occurs.

Figure 2:
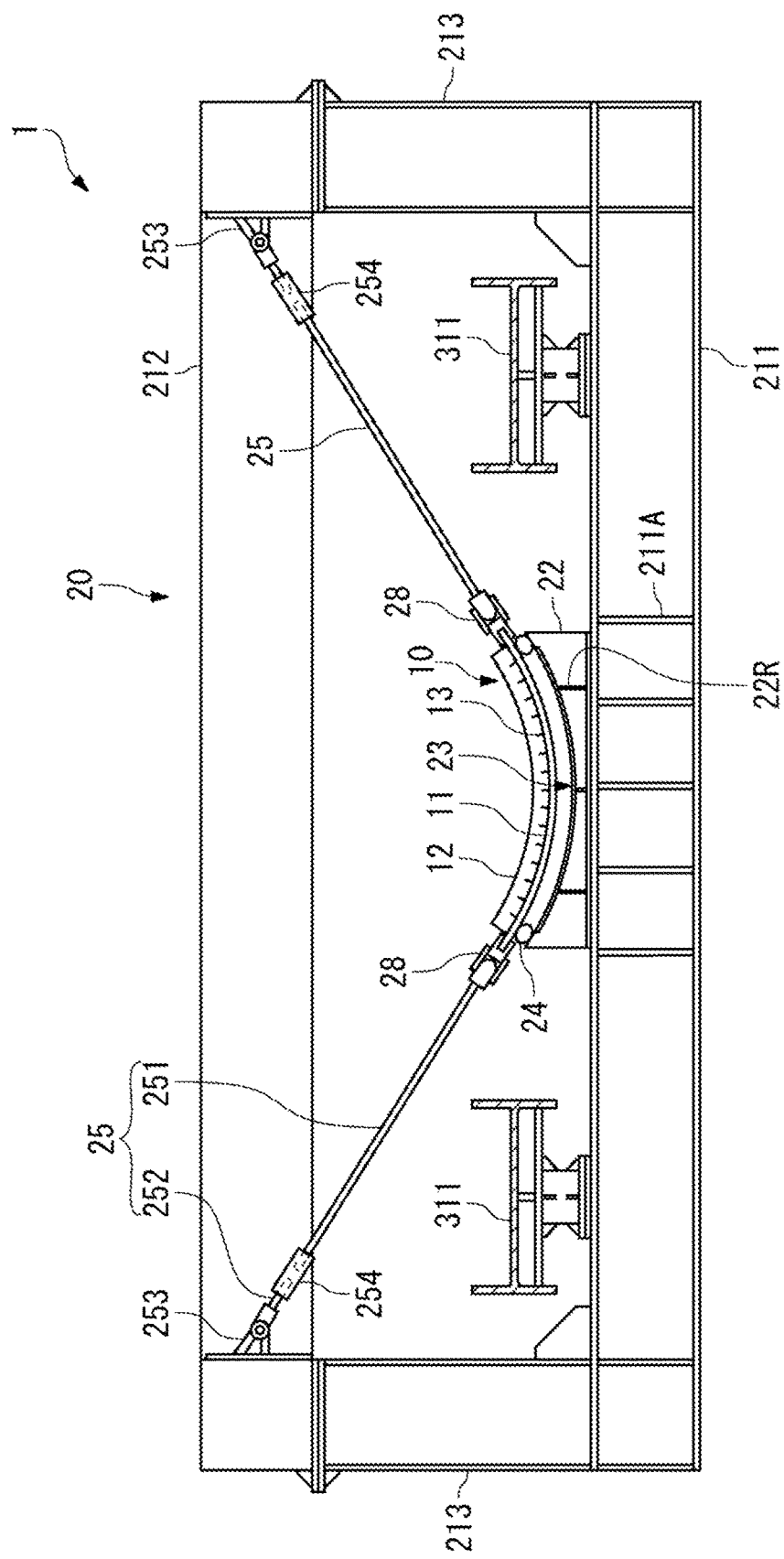
FIG. 2 is a view of the section taken along the line II-II of FIG. 1.

As shown in FIG. 1 to FIG. 3, the internal pressure testing device 20 includes a frame assembly 21, a pressure vessel 22 facing an outer surface 10A of the specimen 10, a sealing member 24 that seals a cavity 23 (space) between the specimen 10 and the pressure vessel 22, a large number of rods (restraining members) 25 that restrain the specimen 10 against an internal pressure applied thereto, a pressure reducing pump 26 that reduces the pressure inside the cavity 23, and a reservoir tank 27.

The frame assembly 21, the pressure vessel 22, and the rods 25 are firmly coupled to one another.

The fuselage of an aircraft is subjected to a tensile force due to the differential pressure between the outside air pressure, which has lowered in the sky, and the cabin pressure.

The main feature of this embodiment is that, to apply an internal pressure equivalent to such a differential pressure to the specimen 10, the pressure inside the cavity 23 faced by the outer surface 10A of the specimen 10 is reduced.

The specimen 10 corresponds to a section of the fuselage to be tested (section to be tested). The section to be tested can be arbitrarily selected from a section provided with an opening, such as a window frame or a maintenance door, a section where members are coupled to each other with a fastener, a general section where there is neither an opening nor a part coupled with a fastener, and the like.

Figure 4A:
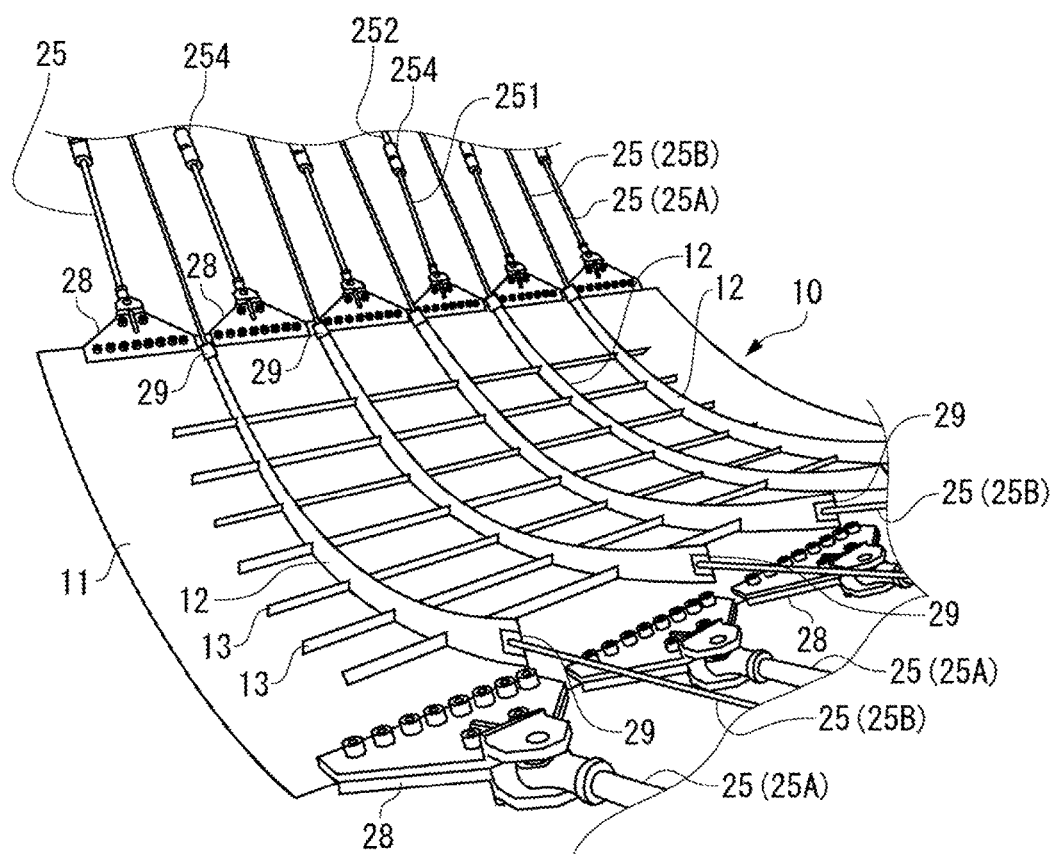
FIG. 4A is a perspective view showing a specimen.

The specimen 10 shown in FIG. 4A corresponds to a general section of the fuselage, and is formed in a circular arc shape in cross-section around the axis line.

The specimen 10 includes a skin 11, a plurality of frames 12 supporting the skin 11 from the inner side, and a plurality of stringers 13 reinforcing the skin 11 from the inner side.

The skin 11 is curved into a circular arc shape so as to be convex from the inner side toward the outer side of the fuselage.

While the end edges of the skin 11 in the circumferential direction are both parallel to the axis line, it is also acceptable that one or both of the end edges are inclined relative to the axis line.

The frames 12 are provided along the circumferential direction on the inner surface of the skin 11.

The stringers 13 are provided along the axial direction on the inner surface of the skin 11.

The skin 11, the frames 12, and the stringers 13 of the specimen 10 of this embodiment are formed from an aluminum alloy, as with those of an actual aircraft. Other metal materials, or fiber reinforced plastics (FRP) containing reinforcing fibers, such as glass fibers or carbon fibers, can also be used as the material of the skin 11, the frames 12, and the stringers 13.

Couplers 28 coupled to the rods 25 are fixed with fasteners at both ends of the skin 11 in the circumferential direction.

Figure 4B:
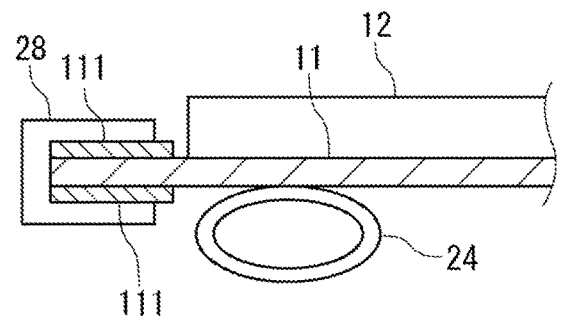
FIG. 4B is a sectional view showing an end portion of the specimen in the circumferential direction.

As shown in FIG. 4B, stiffening plates 111 are laid and fixed on the end portion of the skin 11, where the coupler 28 is provided, from the inner side and the outer side so as to reinforce the end portion. The stiffening plate 111 can be formed in a band-like shape along the longitudinal direction (axial direction) of the skin 11.

Instead of or in addition to providing the stiffening plates 111, the plate thickness of the skin 11 may be increased.

Couplers 29 connected to the rods 25 are fixed with fasteners at both ends of each of the plurality of frames 12 in the circumferential direction.

The frames 12 and the stringers 13 extend to positions closest possible to the end edges of the skin 11, to such an extent as not to interfere with the stiffening plates 111 laid on the skin 11. That is, the part where the frames 12 and the stringers 13 are absent due to the provision of the stiffening plates 111 is minimized.

As shown in FIG. 2, the frame assembly 21 includes a lower frame assembly 211 disposed on the lower side and an upper frame assembly 212 disposed on the upper side. The lower frame assembly 211 and the upper frame assembly 212 are each made of steel and assembled into a rectangular shape in a plan view.

The lower frame assembly 211 is installed on a floor through a stand (not shown). The pressure vessel 22 is provided on the lower frame assembly 211. Reinforcing ribs 211A extending in the vertical direction are formed in a part of the lower frame assembly 211 where the pressure vessel 22 is supported. Similar ribs 22R are formed on the inner side of the pressure vessel 22.

Pillars 213 rise from four corners of the lower frame assembly 211, with the leading ends of the pillars 213 respectively connected to four corners of the upper frame assembly 212.

The upper frame assembly 212 supports the rods 25 restraining the specimen 10.

As shown in FIG. 3, the pressure vessel 22 faces almost the entire region of the outer surface 10A of the specimen 10.

At the peripheral edge of the pressure vessel 22, a sealing part 22B protruding inward relative to the side wall of the pressure vessel 22 is formed. The sealing part 22B has a rectangular shape in a plan view, and the sealing member 24 is disposed on the upper surface of the sealing part 22B.

The cavity 23 is formed between the pressure vessel 22 and the outer surface 10A of the specimen 10.

Here, the outer surface 10A of the specimen 10 facing the pressure vessel 22 is smooth. Unlike the case where the specimen 10 is disposed so that an inner side 10B of the specimen 10 faces the pressure vessel 22 (see FIG. 10), there are no frames 12 and stringers 13 between the specimen 10 and the pressure vessel 22.

In this embodiment, therefore, the interval between the specimen 10 and the pressure vessel 22 is narrowed to such an extent that the specimen 10 does not interfere with the pressure vessel 22 even when the specimen 10 is drawn toward the pressure vessel 22 as the pressure inside the cavity 23 is reduced. Thus, the volume of the cavity 23 is reduced.

Figure 5:
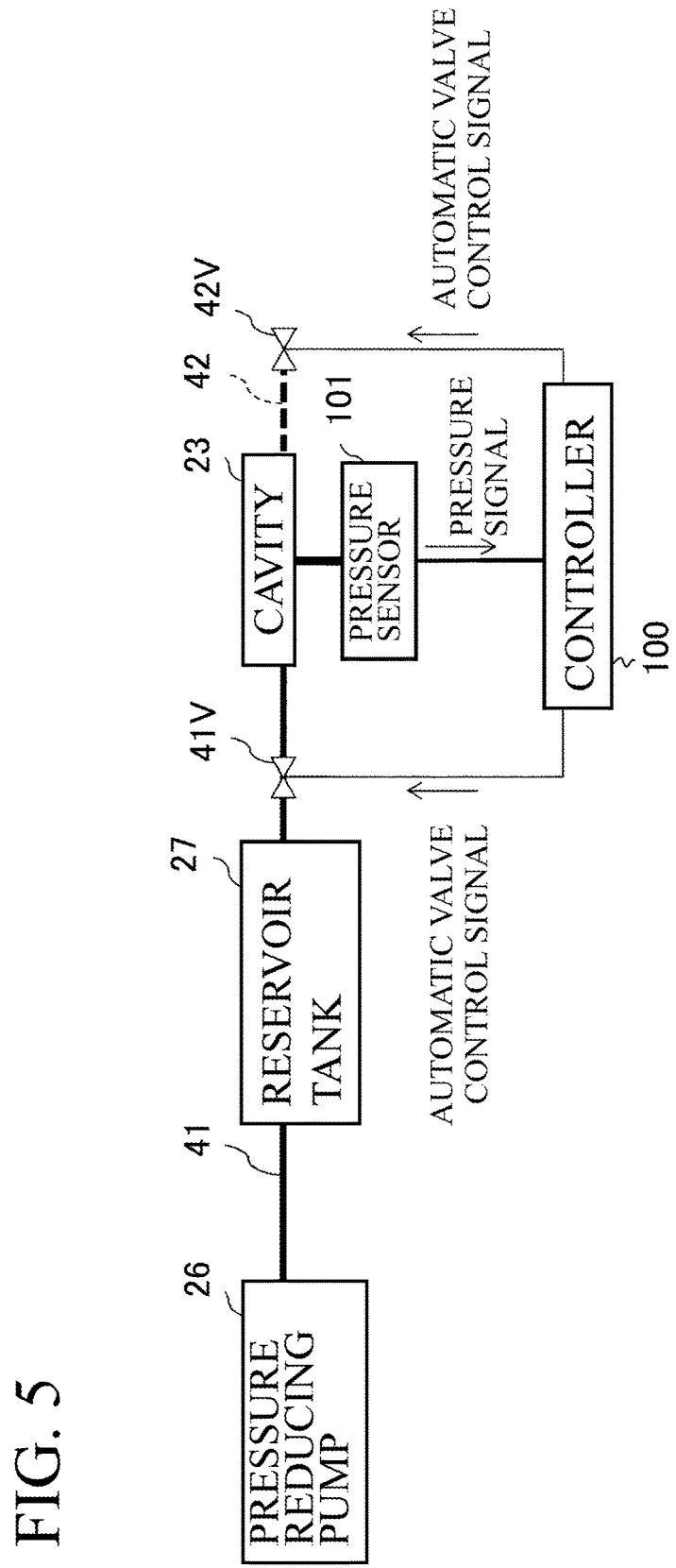
FIG. 5 is a view showing a pressure system that applies an internal pressure.

As shown in FIG. 5, the pressure vessel 22 is provided with a suction path 41 and a release path 42 that lead from the inside of the cavity 23 to the outside of the pressure vessel 22.

The sealing member 24 seals the cavity 23 by being disposed between the sealing part 22B of the pressure vessel 22 and the peripheral edge portion of the outer surface 10A of the specimen 10. The inside of the cavity 23 is faced by almost the entire region of the outer surface 10A of the specimen 10.

Figure 9:
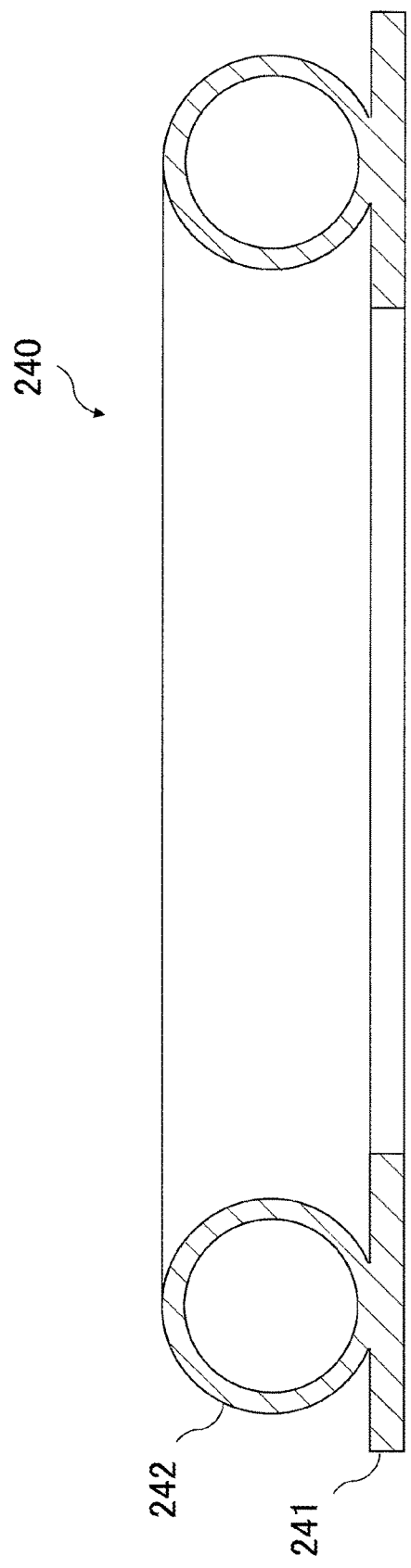
FIG. 9 is a view showing a sealing member according to a modified example of the present invention.

FIG. 3 shows a preferred example of the shape of the sealing member 24 (see FIG. 9). The sealing member 24 in the shape of the letter Ω in cross-section is fixed to the pressure vessel 22 by disposing presser plates 243 on both sides in the width direction of the sealing member 24 and fastening together the presser plates 243, the sealing member 24, and the sealing part 22B. A large number of presser plates 243 are disposed in the longitudinal direction of the sealing member 24.

The sealing member 24 is disposed along the peripheral edge of the specimen 10 in a rectangular annular shape in a plan view.

In the end portion of the specimen 10 in the circumferential direction, the sealing member 24 is disposed at such a position as to retreat from the end edge of the skin 11 beyond the stiffening plates 111 (FIG. 4B) laid on the skin 11.

The sealing member 24 of this embodiment is a hose extruded from an elastic material, such as rubber or elastomer. With both ends of the sealing member 24 connected together, an annular continuous space is created inside the sealing member 24. This space is filled with air at a predetermined pressure. Thus, even in bent portions of the sealing member 24 that are prone to creases, the cavity 23 can be sealed by virtue of the repulsive force of air without leaving any gap between the specimen 10 and the sealing part 22B.

The internal pressure testing device 20 includes a sealing pump 24P that pressurizes the inside of the sealing member 24.

The rods 25 support the specimen 10 that is pulled toward the pressure vessel 22 as the pressure inside the cavity 23 is reduced.

The rods 25 are disposed on both end sides of the specimen 10 in the circumferential direction, along a direction tangential to the end portion of the specimen 10. Then, the presence of a section continuous to the specimen 10 in the circumferential direction in the actual aircraft is simulated by the rods 25, so that the specimen 10 can be restrained in the circumferential direction.

It is preferable that the length and the angle of the rods 25 can be varied in order to maintain the curvature of the specimen 10 without causing a bending stress in the out-of-plane direction on the specimen 10 while the pressure inside the cavity 23 is being reduced.

The rod 25 includes a first rod 251 fixed through the coupler 28 to the end portion of the specimen 10 in the circumferential direction, a second rod 252 fixed through a bracket 253 to the upper frame assembly 212, and a turnbuckle 254 linking the first rod 251 with the second rod 252.

An end portion of the first rod 251 and an end portion of the second rod 252 are screwed into the turnbuckle 254. The end portion of the first rod 251 and the end portion of the second rod 252 have threads in opposite directions. Turning the turnbuckle 254 around the axis can extend or contract the rod 25.

The bracket 253 and the second rod 252 are coupled with a pin to each other. Accordingly, the rod 25 can turn with its upper end as the supporting point, and the angle of the rod 25 to the upper frame assembly 212 can be changed freely.

As shown in FIG. 4A, among the rods 25, some (rods 25A) are coupled through the coupler 28 to the skin 11 between the frames 12, 12 that are adjacent to each other in the specimen 10, while others (rods 25B) are coupled through the coupler 29 to the frame 12.

The coupler 28 has a C-shaped cross-section so as to grip the skin 11 in the thickness direction.

To increase the restraining force of the rod 25 in the axial direction of the specimen 10, the coupler 28 is increased in width gradually from the side coupled to the base end of the first rod 251 toward the side coupled to the skin 11 (in a substantially trapezoidal shape). The coupler 28 is coupled to the skin 11 with a plurality of fasteners that are disposed at intervals in the axial direction.

The coupler 29 has a C-shaped cross-section so as to grip the frame 12 in the thickness direction.

It is desirable that the skin 11 and the frames 12 are restrained by the rods 25A evenly in the axial direction.

Accordingly, it is preferable that the stress on each of the rods 25 and the skin 11 and the frames 12 of the specimen 10 is detected with a strain gauge etc., and the length and the angle of the rods 25 are adjusted on the basis of the stress detected.

Here, to reduce the influence of variation in length or angle of the rods 25 on the stress, the rods 25 are preferably long.

As shown in FIG. 5, the pressure reducing pump 26, the reservoir tank 27, and the cavity 23 constitute a pressure system that applies an internal pressure to the specimen 10. The suction path 41 and the release path 42 of the pressure system are indicated by the thick solid line and the thick dashed line, respectively.

The pressure reducing pump 26 suctions air inside the cavity 23 through the reservoir tank 27 to the outside, and thereby reduces the pressure inside the cavity 23 to a negative pressure of approximately −0.5 atm, for example, relative to the atmospheric pressure.

The reservoir tank 27 is provided along the suction path 41 and stores negative-pressure air. The inside of the reservoir tank 27 functions as a pressure accumulation space.

A pressure reducing valve 41V that opens and closes the suction path 41 is provided between the reservoir tank 27 and the cavity 23.

In this embodiment, the pressure reducing pump 26 is operated, not only while the pressure inside the cavity 23 is being reduced through the suction path 41, but also while the pressure inside the cavity 23 is released into the atmosphere.

Operating the pressure reducing pump 26 with the pressure reducing valve 41V closed can continuously suction air inside the reservoir tank 27 by the pressure reducing pump 26 and reduce the pressure inside the reservoir tank 27.

Then, when the pressure reducing valve 41V is opened, the air inside the cavity 23 is suctioned at once into the reservoir tank 27, in which the pressure has been sufficiently reduced, and thus the pressure inside the cavity 23 can be reduced quickly.

To reduce the flow passage resistance, it is preferable that the diameter of a pipeline connecting the reservoir tank 27 to the cavity 23 is set to be large.

As necessary, a pressure sensor that detects the pressure inside the reservoir tank 27 is provided.

The reservoir tank 27 can also be composed of a plurality of tanks linked with one another.

The release path 42 is provided with a release valve 42V that is opened to release the pressure inside the cavity 23 into the atmosphere.

Opening and closing the pressure reducing valve 41V and the release valve 42V in conjunction with each other can reduce the pressure inside the cavity 23 and release the pressure inside the cavity 23 into the atmosphere.

While the reduction and atmospheric release of the pressure inside the cavity 23 can be performed manually, in this embodiment, automatic valves that can automatically open and close by a control signal are adopted as the pressure reducing valve 41V and the release valve 42V, and a controller 100 that controls the opening and closing actions of the pressure reducing valve 41V and the release valve 42V is provided.

The controller 100 receives a pressure signal indicating the pressure inside the cavity 23 from a pressure sensor 101, and sends a control signal commanding to open or close to each of the pressure reducing valve 41V and the release valve 42V.

As will be described later, the controller 100 also controls the application of an axial force.

A sequencer or a computer can be used as the controller 100.

Next, the axial force testing device 30 will be described.

During flight, the fuselage structure of an aircraft is subjected to a tensile force as it undergoes bending.

The axial force testing device 30 applies an axial force in a tensile direction, simulating such bending, to the specimen 10.

As shown in FIG. 1, the axial force testing device 30 includes a frame assembly 31 having a rectangular shape in a plan view and surrounding the specimen 10 from four sides, and a hydraulic load applicator 32 provided on the frame assembly 31.

The frame assembly 31, the load applicator 32, and the specimen 10 are rigidly coupled to one another.

The specimen 10 is disposed on one end side inside the frame assembly 31, and the load applicator 32 is disposed on the other end side inside the frame assembly 31.

The frame assembly 31 is installed on a floor through a stand (not shown).

The frame assembly 31 includes a pair of beams 311, 311 extending along the axial direction of the specimen 10, an end 312 linking one ends of the beams 311, 311, and an end 313 linking the other ends of the beams 311, 311.

The beams 311, 311 are joined on the upper side of the lower frame assembly 211 (FIG. 2) of the internal pressure testing device 20.

The end 312 is provided with a plurality of wires 33 provided on the skin 11 on one end side of the specimen 10.

The plurality of wires 33 are disposed in parallel to one another along the axis line of the specimen 10.

The load applicator 32 is provided on the end 313.

The load applicator 32 pulls the specimen 10 toward the end 313 by oil pressure. Cooling water is introduced to the inside of the load applicator 32.

The above-described controller 100 sends a control signal commanding to load or unload an axial force to the load applicator 32.

The load applicator 32 is provided at the center of the end 313 along the axis line of the specimen 10. The specimen 10 is coupled to the leading end of the load applicator 32 through a jig 35 and a plurality of wires 34.

The plurality of wires 34 link the skin 11 of the specimen 10 with the jig 35, and are disposed in parallel to one another along the axis line of the specimen 10.

It is preferable that the tensile force of the wires 34 and the aforementioned wires 33 can be appropriately set through the adjustment of their lengths etc.

To transmit an axial force applied by the load applicator 32 evenly in the circumferential direction of the specimen 10, the jig 35 is increased in width gradually from the side coupled to the leading end of the load applicator 32 toward the side coupled to the skin 11.

A publicly-known hydraulic fatigue tester can be used as the load applicator 32.

Next, a case where a fatigue test of applying an internal pressure and an axial force using the combined load testing apparatus 1 is performed will be described with reference to FIG. 6 and FIG. 7.

Figure 7:
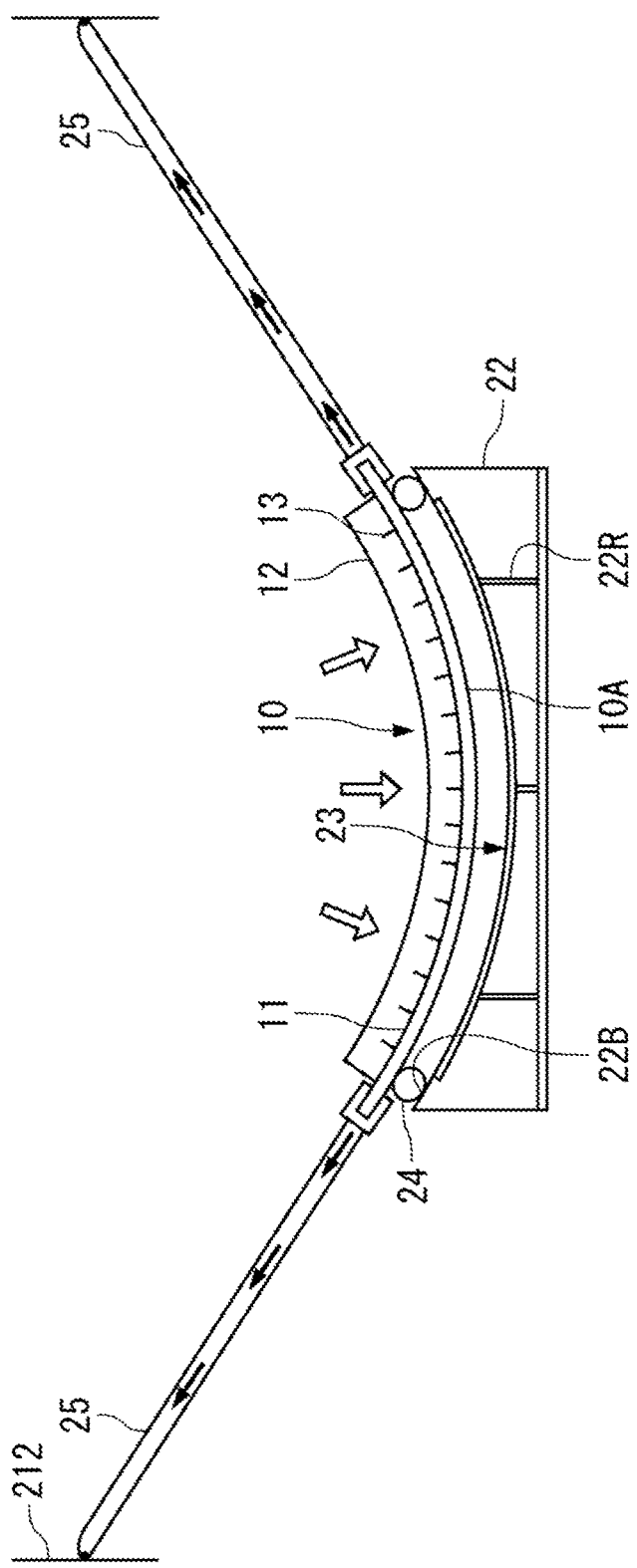
FIG. 7 is a schematic view showing a state in which an internal pressure is applied to the specimen.

First, as shown in FIG. 7, the sealing member 24 is disposed on the pressure vessel 22, and the specimen 10 is disposed on top of that so as to be convex downward. Then, the outer side (outer surface 10A) of the specimen 10 faces the pressure vessel 22, and the inner side of the specimen 10 is exposed.

Figure 6:
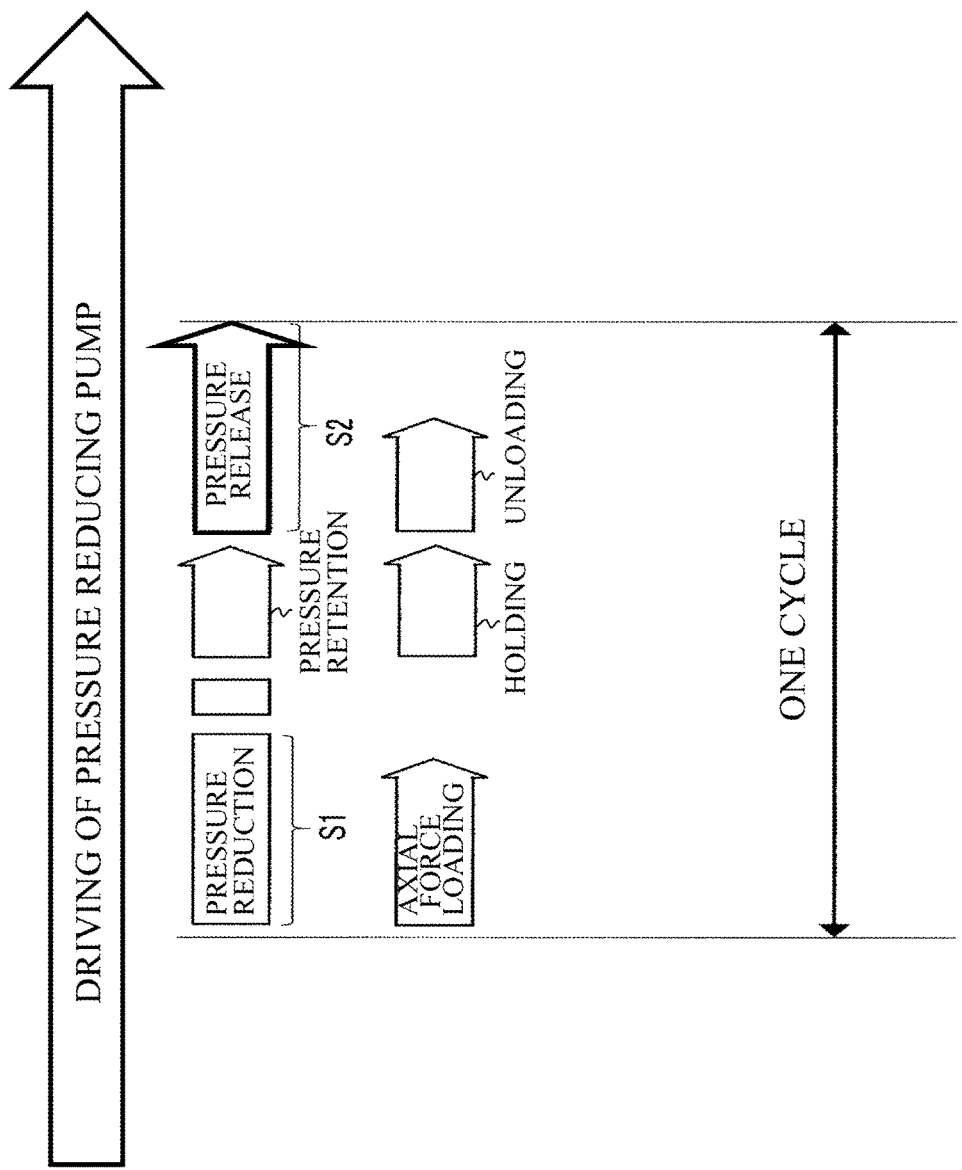
FIG. 6 is a view showing one cycle of a fatigue strength test.

In this embodiment, as shown in FIG. 6, the pressure reducing pump 26 is continuously operated throughout a cycle that includes the reduction and release (atmospheric release) of the pressure inside the cavity 23 and the loading and unloading of an axial force.

Before the cycle is started, the pressure inside the reservoir tank 27 has been sufficiently reduced by operating the pressure reducing pump 26 with the pressure reducing valve 41V closed.

Then, at the start of the cycle, the pressure reducing valve 41V is opened by the controller 100. As a result, the pressure inside the cavity 23 is rapidly reduced by the pressure inside the reservoir tank 27.

Here, the pressure reducing valve 41V may be opened when the detection value of the pressure inside the reservoir tank 27 has reached a predetermined value, or the pressure reducing valve 41V may be opened when a predetermined time determined by prior experiment has elapsed after the operation start of the pressure reducing pump 26.

The controller 100 monitors the detection value of the pressure inside the cavity 23 until it is confirmed that the pressure inside the cavity 23 has reached a specified negative pressure.

Since the volume of the cavity 23 is small as described above, the pressure inside the cavity 23 can be brought to the specified value at once through the reservoir tank 27.

Even if the pressure inside the cavity 23 does not reach the specified negative pressure after suctioning by the reservoir tank 27, air inside the cavity 23 is suctioned continuously thereafter through the reservoir tank 27 by the pressure reducing pump 26, so that the pressure inside the cavity 23 soon reaches the specified value.

It takes a very short time, for example, about several seconds, from the start of the cycle until the completion of pressure reduction to the specified negative pressure.

When the pressure inside the cavity 23 has been reduced, the pressure on the outer side of the specimen 10 (equivalent to the outside air pressure during flight) is lower than the pressure on the inner side thereof (equivalent to the cabin pressure during flight). This is the same as the differential pressure occurring between the inside and the outside of the fuselage of an aircraft in flight. Thus, according to this embodiment, it is possible to perform a test in an environment similar to that of an actual aircraft.

The pressure inside the cavity 23 is a negative pressure relative to the atmospheric pressure, and a pressure (internal pressure) from the inner side toward the outer side in the radial direction is generated on the specimen 10 as indicated by the outlined arrows in FIG. 7. Here, since the frames 12 and the stringers 13 are provided over the entire region of the specimen 10 to which the internal pressure is applied, the skin 11 does not deform in the out-of-plane direction locally in the peripheral edge portion of the specimen 10 due to the internal pressure applied thereto. Thus, a stress can be produced on the specimen 10 evenly in the circumferential direction.

The specimen 10 is restrained by the rods 25 in the circumferential direction of the specimen 10. A reaction force indicated by the thick solid arrows in FIG. 7 acts on the rods 25. Here, since the rods 25 can turn with their upper ends as the supporting point, a bending stress in the out-of-plane direction hardly occurs on the specimen 10. Accordingly, it is possible to reproduce a stress distribution, similar to that when a cylindrical specimen (barrel) is used, over the entire region of the specimen 10 faced by the cavity 23.

Due to the internal pressure applied to the specimen 10, the sealing member 24 is pressed against the specimen 10 and the pressure vessel 22 into close contact therewith. The pressure inside the sealing member 24 can be adjusted so that the sealing member 24 does not buckle.

Concurrently with the application of an internal pressure described above, or after the pressure is reduced to the specified negative pressure, the controller 100 loads an axial force. In this embodiment, the application of an internal pressure and the loading of an axial force are performed at the same time to reduce the test time. The loading of an axial force is performed promptly (e.g., within several seconds) by a command issued to the load applicator 32. The axial force and the above-described internal pressure are applied to the specimen 10 at the same time in superimposition.

Alternatively, the application of an internal pressure and the loading of an axial force can be performed sequentially. Whichever of the application of an internal pressure and the loading of an axial force may be performed first.

After holding the application of an internal pressure and the loading of an axial force for a predetermined time, the controller 100 unloads the axial force, and opens the release valve 42V to release the pressure (pressure release step). These timings can be appropriately determined.

One test cycle is completed when the pressure inside the cavity 23 has returned to the atmospheric pressure or a pressure close to the atmospheric pressure as air escapes through the release path 42.

Subsequently, or after a predetermined time interval, the same cycle is repeated by the controller 100. The number of times of repetition can be calculated on the basis of the durable years and the estimated number of flights of the aircraft, and it is, for example, several hundred thousand times.

While the above cycle is being repeated, any resulting cracks in the specimen 10 and the state of development thereof are observed. The strength of the specimen 10 can be measured, for example, after the application of an internal pressure and the loading of an axial force are held for a predetermined time and before the pressure release step is performed.

Here, since the inner side of the specimen 10 is exposed to the outside of the pressure vessel 22, it is possible to visually observe cracks that can occur in the inner surface (back surface) of the skin 11, the frames 12, and the stringers 13 without using a camera.

Providing the pressure vessel 22 with a window facing the outer side of the specimen 10 (surface of the skin 11) makes it possible to observe the outer side of the specimen 10 through that window. Since the specimen 10 is disposed so as to be convex toward the pressure vessel 22, and since the distance between the window of the pressure vessel 22 and the outer surface 10A of the specimen 10 is short, the outer side of the specimen 10 can also be observed closely.

For example, an evaluation part of the specimen 10 to be evaluated for fatigue strength is set to a predetermined area including a central part of the specimen 10. The fatigue strength can be evaluated by observing this evaluation part.

Since a desired stress distribution equivalent to a stress occurring on the fuselage structure during flight is realized over almost the entire region of the specimen 10, the evaluation part can be set to be a large area of the specimen 10.

Static strength and damage tolerance tests can also be performed by the same procedure as the procedure of the application of an internal pressure and the loading of an axial force having been described above.

As has been described above, in this embodiment, the pressure inside the cavity 23 faced by the outer surface 10A of the specimen 10 is reduced. In principle, possible pressure reduction is 1 atm at the maximum. Thus, without such pressure as to burst the specimen 10 produced inside the cavity 23, the test can be performed safely.

Since the inner side of the specimen 10 is exposed to the outside of the pressure vessel 22, the development of any resulting cracks on the inner side of the specimen 10 is easy to be visually observed.

Moreover, it is possible to minimize the volume of the cavity 23 by bringing the outer surface 10A of the specimen 10 and the inner wall of the pressure vessel 22 close to each other, since there are no frames 12 and stringers 13 inside the cavity 23 that prevent the reduction of the volume of the cavity 23. Then, the time required to apply an internal pressure can be reduced, and the fatigue test can be completed in a short period of time.

In addition, when the pressure inside the cavity 23 is reduced, a force acts in a direction of narrowing the interval between the specimen 10 and the pressure vessel 22, which causes the sealing member 24 to be pressed against the specimen 10 and the pressure vessel 22. Thus, the inside of the cavity 23 can be reliably sealed.

Furthermore, since the sealing member 24 is disposed on the smooth outer side of the specimen 10, the position where the sealing member is provided is not restricted by interference with the frames 12 and the stringers 13. It is not necessary that the frames 12 and the stringers 13 are absent to allow the installation of the sealing member 24, and the frames 12 and the stringers 13 can be provided over the entire region of the specimen 10 to which an internal pressure is applied. Then, it is possible to produce a desired stress on the specimen 10 without causing the peripheral edge portion of the skin 11 to expand in the out-of-plane direction.

Figure 10:
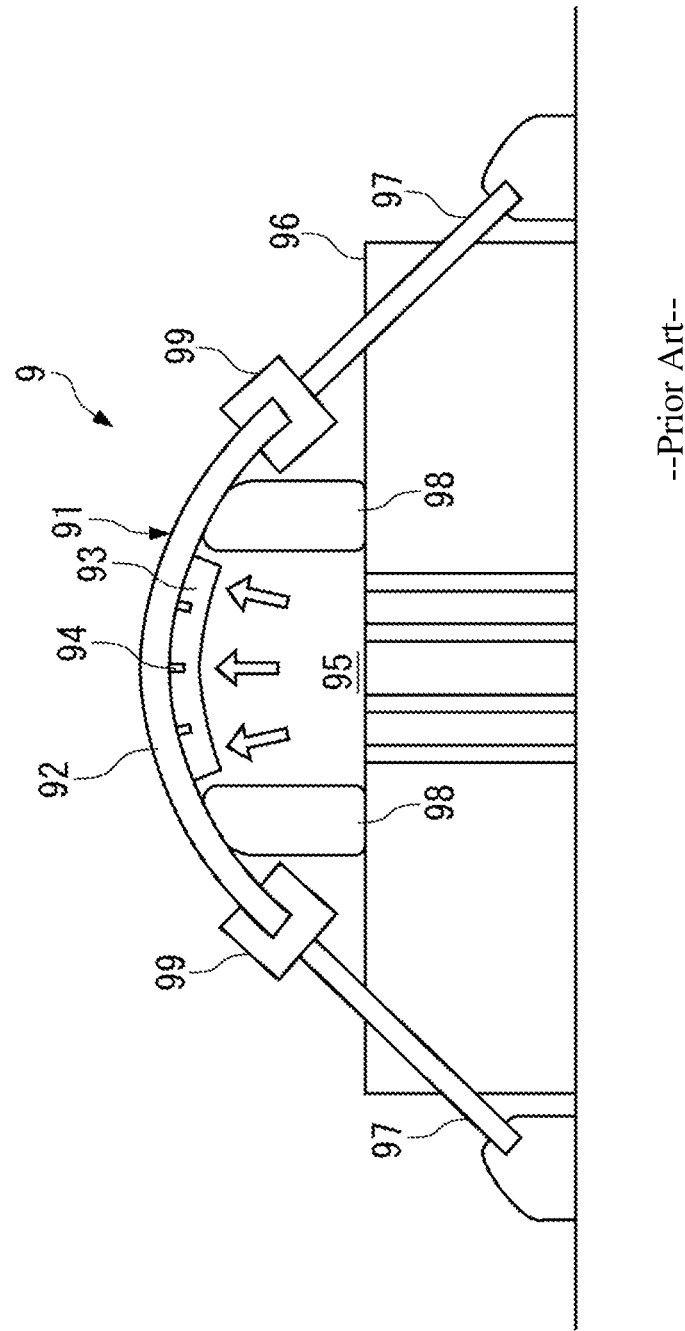
FIG. 10 is a view showing the configuration of an internal pressure test by a conventional pressurization method.

As shown in FIG. 10, the conventional pressurization method requires a large, high-rigidity jig 99 that grips the end portion of the specimen 91 with great force and presses the end portion against the pressure vessel 96. This embodiment does not require such a jig. The couplers 28, 29 used in this embodiment are only required to have the rigidity to reliably couple the specimen 10 and the rods 25 to each other.

When the conventional large jig 99 is used, the jig 99 and the sealing member 98 interfere with each other, which makes it unavoidable to seal at a position away from the peripheral edge portion of the specimen 91. As a result, the pressure receiving region in the specimen 91 is reduced, and the evaluation part is also narrowed.

According to this embodiment, without being forced toward the central part of the specimen 10 due to the jig, the sealing member 24 can seal in the vicinity of the peripheral edge portion of the specimen 10. Since the frames 12 and the stringers 13 are present directly above the sealing member 24, it is possible to realize a desired stress distribution while minimizing an out-of-plane bending stress occurring on the specimen 10.

Thus, the fatigue strength, static strength, and damage tolerance can be evaluated accurately.

Moreover, the device cost can be reduced according to this embodiment, since the pressure reducing pump (vacuum pump) 26 is less expensive than a compressor used in the pressurization method.

In addition, this embodiment achieves a reduction of the cycle time and a reduction of the device cost by using the reservoir tank 27.

As described above, the pressure reducing pump 26 is continuously operated even while the pressure inside the cavity 23 is not being reduced, and a negative pressure is accumulated in the reservoir tank 27 during the extra time when the pressure inside the cavity 23 is not being reduced.

Then, when the pressure reducing valve 41V is opened, the reservoir tank 27 exhibits high suction capacity, so that the pressure inside the cavity 23 can be reduced to a specified pressure in a shorter time. Accordingly, the cycle time can be reduced.

Alternatively, by using the pressure reducing pump 26 of which the suction capacity is not so high, it is possible to secure the sufficient suction capacity to reduce the pressure inside the cavity 23 to a specified pressure by suctioning within a predetermined time while keeping down the cost.

If the volume of the reservoir tank 27 suitable for the capacity of the pressure reducing pump 26 and the test cycle is selected, sufficient effects can be obtained by the above control using the reservoir tank 27. If the volume of the reservoir tank 27 is small relative to the capacity of the pressure reducing pump 26, the pressure range (vacuum range) to which the pressure can be reduced by suctioning of the pressure reducing pump 26 is soon reached, so that thereafter negative pressure cannot be accumulated in the reservoir tank 27 even if the pressure reducing pump 26 is operated. On the other hand, if the volume of the reservoir tank 27 is too large relative to the capacity of the pressure reducing pump 26, the pressure inside the reservoir tank 27 cannot be sufficiently reduced within the extra time when the pressure inside the cavity 23 is not being reduced, which makes it meaningless to operate the pressure reducing pump 26 during the extra time.

Unlike in the conventional pressurization method, the rods 25 do not penetrate the pressure vessel 22, and therefore the structure of the pressure vessel 22 is simple. The man-hours of setting the specimen 10 coupled to the rods 25 in the pressure vessel 22 can also be reduced.

Moreover, since the combined load testing apparatus 1 is a stand-alone type with self-contained force system and electrical system, the testing apparatus can be used simply by installing it in a place where electrical power supply and running water are available.

While the internal pressure testing device 20 is integrated with the axial force testing device 30 in this embodiment, the internal pressure testing device 20 can also be configured as a single device.

Figure 8:
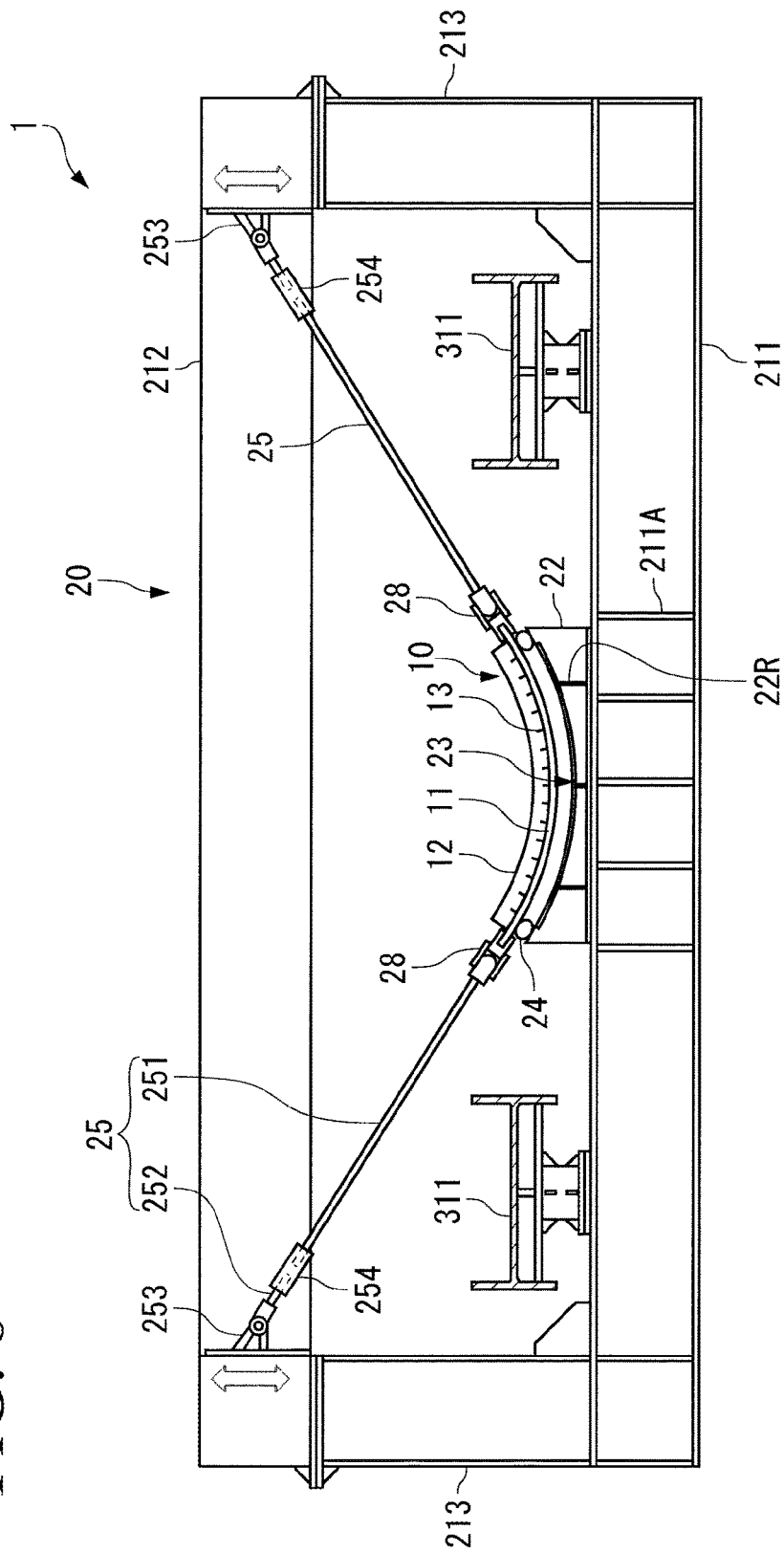
FIG. 8 is a view showing rods according to a modified example of the present invention.

FIG. 8 shows an improved example of the internal pressure testing device 20 of the above embodiment.

The side of the rod 25 supported by the upper frame assembly 212 is movable along the vertical direction as indicated by the outlined arrows in FIG. 8 by a lifting mechanism (not shown) provided on the upper frame assembly 212.

During application of an internal pressure, a bending stress in the out-of-plane direction that, although small, occurs on the specimen 10 due to the restraint by the rods 25 is dissipated as the rods 25 shift upward or downward.

Thus, a stress distribution similar to that when an internal pressure is applied to a barrel can be reproduced.

FIG. 9 shows an improved example of the sealing member that seals the cavity 23.

A sealing member 240 has a fixing part 241 in the form of a band plate disposed on the sealing part 22B (FIG. 3) of the pressure vessel 22, and a cylindrical part 242 provided on the fixing part 241. The sealing member 240 has a cross-sectional shape similar to the letter Ω. The fixing part 241 and the cylindrical part 242 can be integrally formed by extrusion.

When the fixing part 241 is disposed along the sealing part 22B of the pressure vessel 22, the sealing member 240 is positioned relative to the pressure vessel 22.

The upper end of the cylindrical part 242 comes into contact with the peripheral edge portion of the outer surface 10A of the specimen 10. Since the portion between the fixing part 241 and the cylindrical part 242 is constricted, the cylindrical part 242 can swing relative to the fixing part 241.

The inside of the cylindrical part 242 is filled with air at a predetermined pressure.

Depending on the pressure condition inside the cavity 23, the pressure vessel 22 and the specimen 10 are movable relative to each other during application of an internal pressure. In that case, the cylindrical part 242 swings in a direction intersecting with the longitudinal direction of the sealing member 240, and thereby maintains the state of close contact with the outer surface 10A of the specimen 10. Thus, the inside of the cavity 23 can be maintained in the sealed state.

The configurations presented in the above embodiment may be otherwise selectively adopted or appropriately modified into other configurations within the scope of the present invention.

Other than the rods illustrated in the above embodiment, wires, belts, and the like can also be used as the restraining members in the present invention. Ropes formed from glass fibers or carbon fibers can also be used as the restraining members. Fiber ropes can be bonded to the skin, which is formed from fiber reinforced plastics, using a thermosetting or thermoplastic resin. If the specimen is restrained with fiber ropes densely provided at the end edge of the specimen, the restraining force is dispersed and thus the specimen formed from fiber reinforced plastics can be restrained without being damaged.

The sealing member in the present invention does not have to have a hollow part. Even if there is a hollow part, it is not absolutely necessary to fill the hollow part with a gas.

The specimen is not limited to a specimen corresponding to a section of a cylindrical fuselage, and, for example, the specimen may correspond to a pressure partition wall that separates the pressurized compartment of the aircraft from other compartments.

In that case, the shape of the pressure vessel 22 should correspond to the shape of the specimen formed in a dome shape. Then, providing a plurality of rods at the same angle to the center of the specimen can restrain the specimen in a balanced manner along the entire periphery.

REFERENCE SIGNS LIST

1 Combined load testing apparatus
10 Specimen
10A Outer surface
11 Skin
12 Frame
13 Stringer
20 Internal pressure testing device
21 Frame assembly (support member)
22 Pressure vessel
22B Sealing part
22R Rib
23 Cavity
24, 240 Sealing member
24P Sealing pump
25 Rod (restraining member)
25A Rod
25B Rod
26 Pressure reducing pump
27 Reservoir tank
28 Coupler
29 Coupler
30 Axial force testing device
31 Frame assembly
32 Load applicator
33 Wire
34 Wire
35 Jig
41 Suction path
41V Pressure reducing valve
42 Release path
42V Atmospheric release valve
100 Controller
101 Pressure sensor
111 Stiffening plate
211 Lower frame assembly
211A Rib
212 Upper frame assembly (support member)
213 Pillar
243 Presser plate
251 First rod
252 Second rod
253 Bracket
254 Turnbuckle
311 Beam
312 End
313 End
S1 Internal pressure application step
S2 Pressure release step

What is claimed is:

1. An aircraft strength testing apparatus that applies an internal pressure, equivalent to a differential pressure between the outside and the inside of a section to be tested of an airframe of an aircraft, to a curved specimen corresponding to the section to be tested, the testing apparatus comprising:
    a pressure vessel between which and the specimen a cavity is formed; and
    a restraining member that restrains the specimen against the internal pressure, wherein
    the pressure vessel faces the outer side of the specimen, and
    an internal pressure is applied to the specimen by reducing the pressure inside the cavity.

2. The aircraft strength testing apparatus according to claim 1, comprising:
    a pressure reducing pump that reduces the pressure inside the cavity by suctioning;
    a tank provided on a suction path connecting the pressure reducing pump to the cavity; and
    a valve that is located between the tank and the cavity, and opens and closes the suction path.

3. The aircraft strength testing apparatus according to claim 2, wherein the specimen is disposed so as to be convex toward the pressure vessel.

4. The aircraft strength testing apparatus according to claim 1, wherein
    a sealing member that seals the cavity is disposed between the specimen and the pressure vessel, and
    the inside of the sealing member is filled with a gas at a predetermined pressure.

5. The aircraft strength testing apparatus according to claim 4, wherein the sealing member is a hose formed from an elastic material.

6. The aircraft strength testing apparatus according to claim 1, wherein the specimen is disposed so as to be convex toward the pressure vessel.

7. The aircraft strength testing apparatus according to claim 1, wherein
    the outer side of the specimen facing the pressure vessel is smooth, and
    the inner side of the specimen is exposed outside the pressure vessel.

8. The aircraft strength testing apparatus according to claim 1, comprising a support member that supports the restraining member, wherein the restraining member is coupled with a pin to the support member.

9. The aircraft strength testing apparatus according to claim 1, comprising a support member that supports the restraining member, wherein a side supported by the support member in the restraining member is movable in the out-of-plane direction of the specimen.

10. The aircraft strength testing apparatus according to claim 1, wherein
    the specimen includes a skin, a frame supporting the skin, and a stringer reinforcing the skin,
    a sealing member that seals the cavity is disposed in a peripheral edge portion on the outer side of the skin, and
    of the frame and the stringer, at least the frame is present at a position on the inner side of the skin corresponding to the position of the sealing member.

11. The aircraft strength testing apparatus according to claim 1, comprising a device that applies an axial force along an axis line to the specimen that is formed in a circular arc shape in cross-section around the axis line.

12. An aircraft strength testing method using a specimen, the specimen being a curved specimen corresponding to a section to be tested of an airframe of an aircraft, the testing method comprising an internal pressure application step of applying an internal pressure, equivalent to a differential pressure between the outside and the inside of the section to be tested, to the specimen by applying a negative pressure to the inside of a cavity faced by the outer side of the specimen, wherein prior to the internal pressure application step, a step of restraining the specimen against the internal pressure is conducted.

13. The aircraft strength testing method according to claim 12, wherein the cavity is a space formed between the specimen and a pressure vessel that is disposed so as to face the outer side of the specimen.

14. The aircraft strength testing method according to claim 12, wherein the source of application of the negative pressure is a pressure reducing pump.

15. An aircraft strength testing method using a specimen, the specimen being a curved specimen corresponding to a section to be tested of an airframe of an aircraft, the testing method comprising:

a step of restraining the specimen against an internal pressure, equivalent to a differential pressure between the outside and the inside of the section to be tested;

an internal pressure application step of applying the internal pressure to the specimen by applying a negative pressure to the inside of a cavity faced by the outer side of the specimen; and a pressure release step of returning the pressure inside the cavity, to which the negative pressure has been applied, to an atmospheric pressure or a pressure close to the atmospheric pressure, wherein one cycle including at least the internal pressure application step and the pressure release step is repeated a predetermined number of times of cycles.

16. The aircraft strength testing method according to claim 15, wherein a pressure reduction step of accumulating a negative pressure in a pressure accumulation space located in a stage preceding the cavity by reducing the pressure inside the pressure accumulation space is performed while the pressure release step is being performed, and in the internal pressure application step, the negative pressure accumulated in the pressure reduction step is introduced into the cavity.

17. The aircraft strength testing method according to claim 16, wherein the cavity is a space formed between the specimen and a pressure vessel that is disposed so as to face the outer side of the specimen.

18. The aircraft strength testing method according to claim 16, wherein the source of application of the negative pressure is a pressure reducing pump.

19. The aircraft strength testing method according to claim 15, wherein the cavity is a space formed between the specimen and a pressure vessel that is disposed so as to face the outer side of the specimen.

20. The aircraft strength testing method according to claim 15, wherein the source of application of the negative pressure is a pressure reducing pump.

* * * * *